United States Patent [19]

Fog et al.

[11] Patent Number: 4,632,732
[45] Date of Patent: Dec. 30, 1986

[54] ION-SELECTIVE MEASURING ELECTRODE DEVICE AND METHOD FOR MEASURING HYDROGEN ION

[75] Inventors: Agner Fog, Copenhagen; Sven H. K. Atlung, Holte, both of Denmark

[73] Assignee: Radiometer A/S, Copenhagen, Denmark

[21] Appl. No.: 557,161

[22] PCT Filed: Mar. 15, 1983

[86] PCT No.: PCT/DK83/00035
§ 371 Date: Nov. 15, 1983
§ 102(e) Date: Nov. 15, 1983

[87] PCT Pub. No.: WO83/03304
PCT Pub. Date: Sep. 29, 1983

[30] Foreign Application Priority Data

Mar. 15, 1982 [DK] Denmark ............................. 1132/82

[51] Int. Cl.$^4$ ..................... G01N 27/36; G01N 27/46
[52] U.S. Cl. .................................. 204/1 T; 204/416; 204/419; 204/420

[58] Field of Search ............... 204/416, 418, 419, 420, 204/1 T

[56] References Cited

U.S. PATENT DOCUMENTS

| | | | |
|---|---|---|---|
| 3,825,482 | 7/1974 | Wechter et al. | 204/419 |
| 3,853,731 | 12/1974 | Gray et al. | 204/420 |
| 3,856,634 | 12/1974 | Hahn et al. | 204/1 T |
| 4,111,777 | 9/1978 | Dobson et al. | 204/419 |

Primary Examiner—G. L. Kaplan
Attorney, Agent, or Firm—Stiefel, Gross, Kurland & Pavane

[57] ABSTRACT

An ion selective electrode device, in particular a pH-sensitive electrode device, employing an intercalation electrode (3) as contact material between an ion selective element (2) and an electrical connection (9).

An intercalation electrode comprising an equilibrium mixture of two phases, at least one of the phases working as an intercalation electrode, is disclosed.

The electrode device may be constructed as a solid state electrode device showing advantageous electrode properties.

17 Claims, 8 Drawing Figures

ION-SELECTIVE MEASURING ELECTRODE DEVICE AND METHOD FOR MEASURING HYDROGEN ION

TECHNICAL FIELD

The invention relates to an ion selective electrode device. In particular, the invention relates to the use of a solid material which is conductive for certain metal ions and for electrons and which comprises an intercalation electrode for the metal ions in question in an ion selective electrode device as a contact material between an electrical connection and an ion selective element comprising the metal ions, the said ion selective electrode showing selectivity towards hydrogen ions or other ions, which differ from the said metal ions.

BACKGROUND ART

The use of solid contact materials in ion selective electrode devices between an ion selective membrane and an inner reference electrode is well known and literature covering this topic is comprehensive. For example, the specifications of U.S. Pat. Nos. 2,117,596 and 3,853,731, respectively, and the specification of DE patent application No. 2220841 laid open to public inspection deal with solid contact materials. The measuring electrode devices described are disadvantageous therein that the electrochemical processes which take place in the contact material are not as effective and well-controlled as necessary to ensure stable measurement results.

Solid lithium-containing contact materials have been employed in pH electrode devices having a pH sensitive membrane of lithium containing glass. These electrode devices are disclosed in the specification of SU Pat. No. 759943 (Shul'ts) and in connection with a study concerning the stability of ion selective measuring electrode devices in Shul'ts M. M.: Journal of Applied Chemistry of the USSR, 52 (11), 2354 (1980).

Previously, intercalation electrodes have been used for other electrochemical purposes, e.g. in electrical batteries and in electrochemical measuring electrode devices of another type than the measuring electrode device according to the present invention.

The use of the materials in electrical batteries is i.a. disclosed in Whittingham M. S.: Journal of the Electrochemical Society, 123 (3), 315 (1976) and in Murphy D. W., Christian P. A.: Science 205 (4407), 651 (1971).

As far as the group of intercalation materials characterized as bronzes is concerned, the use of solid materials functioning as intercalation electrodes in measuring or reference electrode devices is i.a. disclosed in the specifications of the patents indicated below:

SU Pat. No. 834491—Dokuchaev L. Ya. et al.
SU Pat. No. 785720—Volkov V. L. et al.
SU Pat. No. 723447—Koksharova I. U. et al.
SU Pat. No. 468893—Koksharov A. G. et al.
U.S. Pat. No. 3,878,059—Wechter M. A. et al.
SU Pat. No. 293493—Volkov V. L. et al.
U.S. Pat. No. 3,856,634—Hahn P. B. et al.
U.S. Pat. No. 3,825,482—Wechter M. A. et al. In addition to these patents further publications relating to the same topic are the following:

Koksharova I. U. et al.: Issled. Stroeniya i Svoistv Oksidn. Soedin. d i f Elementov, Sverdlovsk, p. 47–49 (1980)

Koksharova I. U. et al.: Akad. Nauk SSSR 31, 68–69 (1975)
Koksharova I. U. et al.: Funkts. organ soedin. i polimery, p. 219–221 (1974)
Koksharova I. U. et al.: Khimiya i tekhnol. vanadievykh soedin., p. 304–306 (1974)
Volkov V. L. et al.: Funkts. Org. Svedin. Polim., p. 177–179 (1973)
Koksharov A. G. et al.: Akad. Nauk SSSR, 25, 85–88 (1973)
Hahn P. B.: Diss. Abstr. Int. B., 34(7) 3137 (1974) (Abstract)
Hahn P. B. et al.: Anal. Chem., 46(4), 553 (1974)
Hahn P. B.: NTIS-report No. IS-T-597 (1973)
Randin J. P. et al.: J. Electrochem. Soc., 120(9), 1174 (1973)
Hahn, P. B. et al.: Anal. Chem., 45(7), 1016 (1973)
Wechter M. A. et al.: Anal. Chem., 45(7), 1267 (1973)
Wechter M. A. et al.: Anal. Chem., 44(4), 850 (1972)
Koksharov A. G.: Perm. Gos. Univ., 178 117 (1968)
Koksharov A. G. et al.: Uch. Zap., Perm. Cos. Univ., 111, 63 (1964)
Ibid: 178, 117 (1968)
Koksharov A. G. et al.: Izv. Vyssh. Ucheb. Zaved. Khim. Khim. Tekhnol., 10, 243 (1967)

It is a common feature of the electrode devices disclosed in above-mentioned publications and comprising bronze intercalation compounds that they are used as reference electrodes or that the bronze intercalation compound per se is the measuring electrode, the electrode potential being determined by a redox process involving the bronze intercalation compound and the ion to be measured by the electrode device.

The above-mentioned electrode devices are rather unsuitable for pH-determination, cf. Wechter, Anal. Chem. 44 851 (1972) stating that the electrode devices disclosed are not useful in the direct determination of pH, this statement being based on comparison experiments showing a better linearity for glass electrodes than for bronze electrodes. Moreover, electrode devices based on bronze intercalation compounds as the sensitive material are unsuitable for some applications, these compounds being unstable on contact with aqueous solutions.

The use of bronze intercalation compounds intercalating the type of ions for which the activity is to be measured in ion selective electrode devices apart from pH electrodes is disclosed in the specification of DE patent application No. 2538739 laid open to public inspection. In the said specification an embodiment having a $\beta$-alumina membrane between the sample and the bronze intercalation electrode has been disclosed. However, the relationship between this membrane and the selectivity of the electrode device is not clearly disclosed.

The object of the invention is to provide ion selective electrode devices which may be constructed as solid state ion selective electrode devices and which as regards the well known electrode properties such as sensitivity and stability compare to or are superior to the prior art ion selective electrode devices. In particular, the object of the invention is to provide pH measuring electrode devices.

Solid state measuring electrode devices are advantageous in many respects and for years it has been a desire to make available solid state electrode devices suited for replacing the prior art electrode devices containing an inner liquid. The solid state electrode devices may be used for a wider temperature range than the electrode devices containing a liquid; they may be arbitrarily oriented, and they are suitable for miniaturization which is of interest in connection with physiological or biochemical applications.

However, to make solid state measuring electrode devices an intersecting alternative to electrode devices containing a liquid the electrode properties should compare to those of the liquid containing electrode devices.

DISCLOSURE OF THE INVENTION

The ion selective electrode device according to the invention comprises an ion selective element showing ion exchange properties and containing metal ions which on normal use of the electrode device are exchanged with the ions to which the electrode device shows selectivity, an electrical connection and a solid material providing electrical contact between the ion selective element and the electrical connection, the electrode device being characterized in that the solid material comprises a material acting as an intercalation electrode for the metal ions and that the metal ions differ from the ion to which the electrode device shows selectivity.

Any suitable ion selective element may be selected for the ion selective element. Thus, it is envisaged that organic as well as inorganic ion selective elements may be used in the electrode device according to the invention. Furthermore, any suitable electronic conductive material which may be connected to the analyzing equipment used together with the electrode device may be used as the electrical connection. Usually, the connection will be established by means of an electronic conductor in a cable.

However, it is also possible to make constructions which are more compact. Possibly, the electrical connection and the solid contact material may be constructed from the same material and may form an integral structure.

For many purposes, however, a metal wire will be suitable as the electrical connection or part of it.

Moreover, a liquid more or less viscous electrolyte or a solid crystalline or amorphous ionic conductive material containing the metal ions may be inserted between the ion selective element and the solid contact material. According to the invention the solid material providing the electrical contact between the ion selective element and the electrical connection is a material which functions as an intercalation electrode for the metal ions.

In the present context the terms "intercalation electrode" and "intercalation compound" are used as the name for a crystalline material having the following properties:
  the material shows ionic conductivity as far as certain ions are concerned;
  the material shows electronic conductivity;
  the crystal structure of the material provides sites into which the ions in question may enter without displacing other ions or atoms;
  the material is able to incorporate or give off electrons and ions of said type through a redox process which takes place internally in the material or at the surface thereof.
  the content of said ions may be reversibly varied in the material within certain limits by the above mentioned redox process without the formation or cleavage of any covalent bonds of appreciable strength and without any appreciable changes in the crystalline structure of the material.

Besides the terms "intercalation electrode" and "intercalation compound" the terms "insertion electrode" or "solid solution electrode" is used in the literature for these materials. Further definition of the materials is given in the publications mentioned on page 2 of Whittingham and of Murphy and Christian, respectively.

Examples of intercalation compounds are: $Li_xV_2O_5$, $Li_xV_6O_{13}$, $Li_xTi S_2$, $Li_xWO_3$, $Na_xWO_3$, where x is a number which may vary within a certain range, and other bronze materials of the oxide type.

The ion selective electrode devices according to the invention may further comprise elements such as e.g. an external reference electrode structure, other electrochemical measuring electrode means, transducers of other kinds, e.g. temperature sensors, and signal amplifying means.

The theoretical back-ground of the invention will not be explained in details herein. However, it should be emphasized that the advantageous electrode properties depend on the possibility of reversible transport of certain metal ions across the boundary between the ion selective element and the solid contact material and reversible transport of electrons across the boundary between the solid contact material and the electrical connection and the reversible interaction between ions and eletrons in the solid contact material.

Solid state ion selective electrode devices for pH-measurements showing advantageous electrode properties have been disclosed previously, cf. Shul'ts: Journal of Applied Chemistry in the USSR, 52(11), 2354 (1980). The electrode devices disclosed herein are glass electrodes having a pH-sensitive glass membrane containing lithium or sodium. Two types of electrode devices have been disclosed. One of these is provided with metallic lithium or sodium on the inner side of the lithium respective sodium containing glass membrane. As fas as stability is concerned these electrode devices are excellent. For practical applications, however, they are considered inapplicable in connection with measurements in aqueous solutions due to the potential danger of a heavy reaction between the metallic contact material and the solution on breakage of the glass membrane. In the other type the pure alkali metal material is replaced by a contact material showing reduced activity of the alkali metal. It is stated that very stable electrode devices may be prepared using these materials, which are not further defined.

In a preferred embodiment the intercalation electrode comprises an equilibrium mixture of two phases at least one of which functions as an intercalation electrode for the metal ions. In the equilibrium mixture the chemical potential of the metal ion is fixed and in consequence thereof the stability of the measurements performed by the electrode device is increased. For a better understanding of the advantages obtained when using a two phase system for the intercalation electrode in the electrode device according to the invention there is referred to the detailed part of the specification dealing with FIG. 5.

Especially in connection with ion selective elements containing lithium ions it is preferred to use an intercalation electrode comprising lithium vanadium bronze. In that case the ion selective elements in question may be made from pH-sensitive glasses or sodium sensitive glasses. Also lithium sensitive glasses containing lithium are known.

Lithium vanadium bronze having $\beta$- or $\beta'$-structure and of the composition $Li_xV_2O_{5-y}$, wherein $0.22 < x < 0.47$ and $0 < y < 0.05$ is especially preferred due to the particularly suitable properties of these compounds. The compounds are described in J. Galy et al.: Revue de Chimie minerale, B, 509 (1971), and possess the following advantageous properties:

high ionic conductivity;
high electronic conductivity;
chemical resistance to water, air and a great number of chemicals;
resistance to very high as well as very low temperatures;
ability to bond to a glass membrane by melting or sintering;
easy preparation and handling.

Especially lithium vanadium bronze having the composition $Li_xV_2O_{5-y}$, wherein $0.37 < x < 0.44$ and $0 < y < 0.05$ is preferred for use in the intercalation electrode in the electrode device according to the invention. Based on this material as starting material it is possible to establish an equilibrium between two phases comprising $Li_{0.37}V_2O_5$ and $Li_{0.44}V_2O_5$, respectively, thereby fixing the chemical potential of the lithium ions as also explained in general terms previously.

Preparation of lithium vanadium bronze of the composition $Li_xV_2O_5$ is described in P. G. Dickens et al.: Solid State Ionics 2, 27 (1981). The compounds of the composition $0.37 < x < 0.44$ form spontaneously on cooling from 500° C. to room temperature a mixture of the $\beta$-phase and the $\beta'$-phase ($Li_{0.37}V_2O_5$ and $Li_{0.44}V_2O_5$).

Since intercalation compounds are known which may be bonded to a glass membrane by melting or sintering, a glass membrane is suitable as the ion selective element in the electrode device according to the invention.

Glass membranes made from silica glass containing lithium ions are usable in connection with intercalation compounds containing lithium. This is because of the fact that these membranes exchange in a manner known per se the ion to which they are selective with lithium ions, lithium ions being incorporated in the lithium containing intercalation compound under reaction with electrons, cf. FIG. 4 and the part of the specification dealing with FIG. 4.

Among the ion selective lithium containing silica glasses should be mentioned a glass used in pH-electrode devices manufactured by RADIOMETER A/S, Copenhagen, and designated C-glass.

The invention also relates to a method of preparing an ion selective electrode device comprising an ion selective element, an electrical connection and a solid contact material between the electrical connection and the ion selective element, the said measuring electrode device being characterized in that the ion selective element is made from a pH-sensitive silica glass containing lithium ions, that the solid contact material is made from a lithium vanadium bronze material and that the ion selective element and the solid contact material are sintered or melted together.

An ion selective electrode device having a layer of solid contact material adhered to the ion selective element is obtained thereby.

However, working electrode devices according to the invention may also be prepared without the sintering step. In that case care should be taken to ensure adequate transfer conditions between the ion selective element and the solid contact material.

The invention will now be further explained with reference to the drawings and the appended examples.

Figure 1:
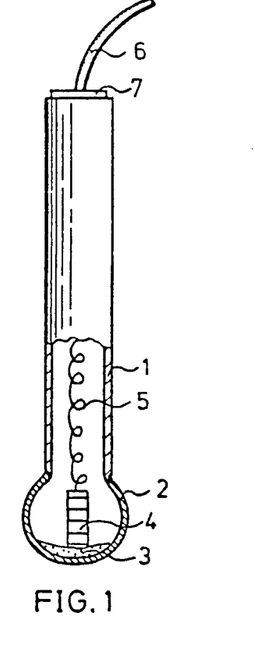
FIGS. 1-3 are schematic illustrations of various embodiments of the measuring electrode device according to the invention.

The electrode device according to FIG. 1 is an embodiment from the experimental stage of the development course.

The electrode device of FIG. 1 comprises a tube 1 of lead glass to which an ion selective bulb-shaped glass membrane 2 of lithium containing silica glass is melted. A solid powdered material 3 is placed in the bottom of the bulb, the said material functioning as an intercalation electrode. An ion conducting liquid film (not shown) is provided between the membrane 2 and the powdered material to ensure adequate ion transfer conditions.

In electrical contact with the intercalation electrode a rod of an electrically conducting material 4 is provided. The material 4 is fixed against the intercalation electrode 3 by means of a bronze spring 5, the opposite end of which is soldered to an electrical conductor in the electrode cable 6 which is a cable shielded against electrical noise. The interior of the electrode device is filled with an inert gas and the open end of the tube 1 is sealed by a wax stopper 7.

Figure 2:
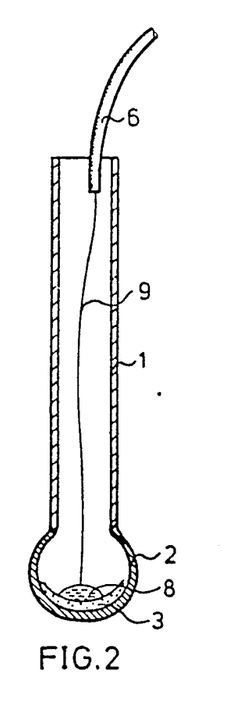

The embodiment shown in FIG. 2 for the electrode device according to the invention is also an electrode of a preliminary design.

The electrode device comprises a tube 1, an ion selective bulb-shaped glass membrane 2 and a solid contact material 3 comprising $Li_{0.38}V_2O_5$. The solid contact material is sintered to the inner side of the bulb-shaped glass membrane 2. Accordingly, the ionic conductive liquid film in the electrode device according to FIG. 1 is superfluous in the embodiment according to FIG. 2. An electrical connection 9 is via an electrically conductive silver epoxy 8 in electrical contact with the solid contact material 3 and at the opposite end connected to a shielded electrode cable 6.

Figure 3:
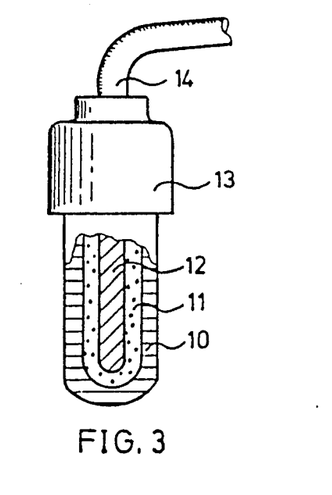

The embodiment shown in FIG. 3 for the electrode device according to the invention is of a more compact type and may be suitable for production on a commercial scale. The electrode device shown comprises an ion selective element 10 with a centrally located electrical connection 12. Between this electrical connection and the ion selective element an intercalation electrode 11 is interlayered. The electrical connection is connected to a conductor in a shielded electrode cable 14. An electrically insulating enclosure 13 surrounds the upper end of the electrode device and a segment of the electrode cable 14.

Figure 4:
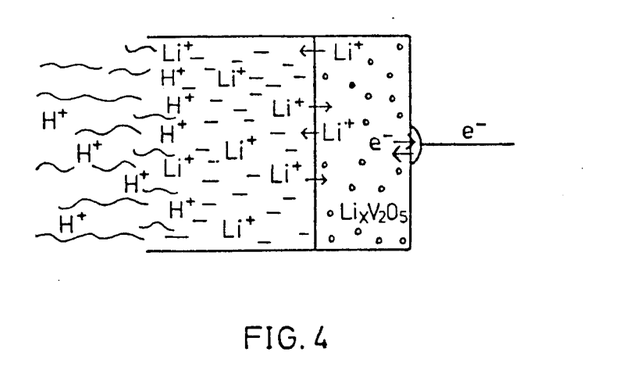
FIG. 4 illustrates the electrochemical conditions in a pH-sensitive electrode device according to the invention.

FIG. 4 illustrates the electrochemical conditions in a pH-sensitive lithium containing silica glass having one surface interfacing a sample and another surface interfacing an intercalation electrode for lithium ions, in casu $Li_xV_2O_5$.

Hydrogen ions drawn into the glass from the sample cause a flow of lithium ions into the intercalation electrode. The positively charged lithium ions are incorporated in the intercalation electrode. Thereby, a corresponding amount of electrons are bound, giving rise to the development of a potential on the measuring electrode device.

Due to the special properties of the intercalation electrode the electrons necessary for the electrode reaction can easily be supplied via the intercalation electrode and the electrical connection and ensure the obtainment of an equilibrium state in the system. The obtainment of an equilibrium state is a prerequisite for the achievement of stable electrode potential measurements.

Figure 5:
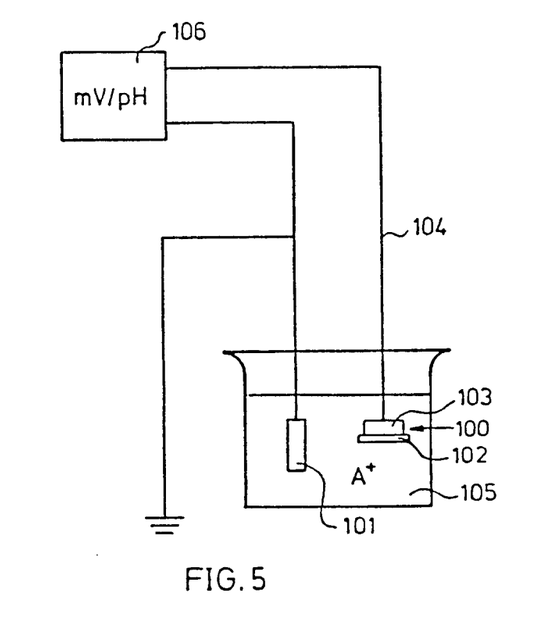
FIG. 5 illustrates the electrochemical back-ground of the invention.

FIG. 5 shows diagrammatically a measuring system. An ion selective electrode device generally designated 100 and a reference electrode 101 are placed in a soluton 105 containing ions $A^+$ to which the ion selective measuring electrode device 100 is selective.

The measuring electrode device comprises an ion selective element 102, an intercalation compound 103 and a conductor 104.

The measuring electrode device is connected to one input means of a pH/mV-meter, and the reference electrode, the potential of which is defined in a suitable manner, in casu by grounding, is connected to another input means.

For a suitable measuring electrode device the electrical potential measured by the mV-meter 106 should be related to the activity of $A^+$ in the sample in a simple manner.

The relationship can be expressed by the equation:

$$\phi^{103} - \phi^{105} = C - \frac{\mu_{B+}^{103}}{z_2 F} + \frac{RT}{z_1 F} \ln a_{A+}$$

wherein
$\phi 103$ is the electrical potential of the intercalation electrode;
$\phi 105$ is the electrical potential of the sample;
C is a constant;
$\mu_{B+}^{103}$ is the chemical potential of the ion $B^+$ in the intercalation electrode;
$Z_1$ is the charge number for the ion $A^+$ in the sample;
$Z_2$ is the charge number for the ion $B^+$ in the intercalation electrode;
F is the Faraday number;
R is the gas constant;
T is the temperature in degrees K.;
$a_{A+}$ denotes the activity of the ion $A^+$ in the sample;
$\mu_{B+}^{103}$ can be be fixed by using as the intercalation electrode a system comprising two phases which are chemically in equilibrium. In that case the potential measured will in a straightforward way reflect the activity of the ion $A^+$ in the sample.

Figure 6:
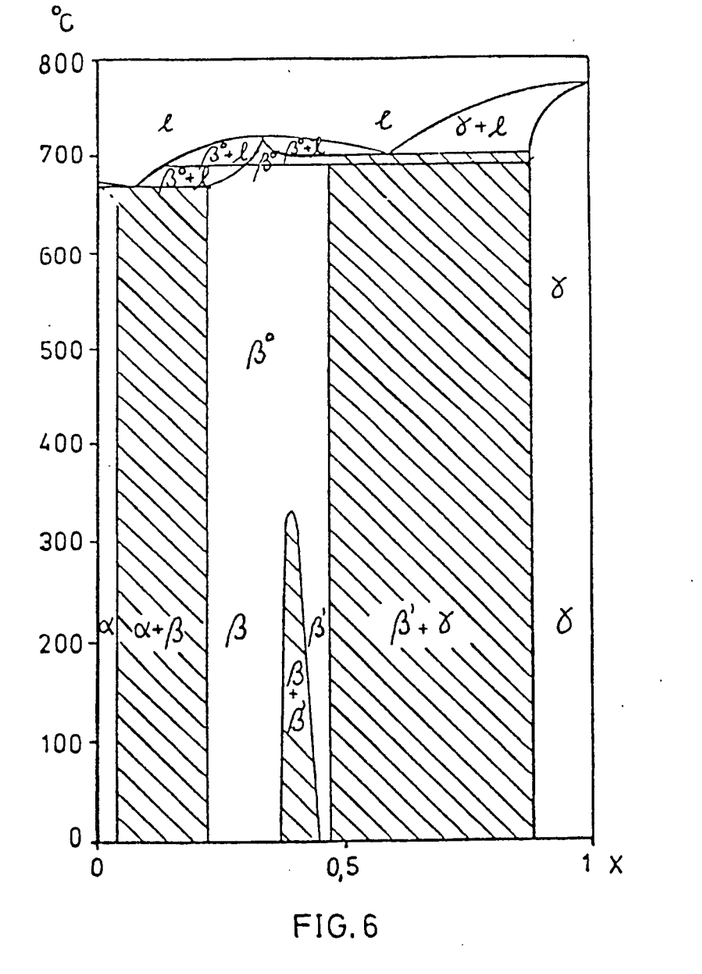
FIG. 6 shows the phase diagram of a preferred intercalation compound according to the invention.

FIG. 6 is a phase diagram showing the varying crystal structures of $Li_xV_2O_5$ for $0<x<1$. It appears from FIG. 6 that in the range $0.37<x<0.44$ an equilibrium mixture of the two crystal forms $\beta$ and $\beta'$ exists. Furthermore, the transformation between the two crystal forms $\beta$ and $\beta'$ takes place very quickly at room temperature. Accordingly, it is theoretically contemplated that $Li_xV_2O_5$ with $0.37<x<0.44$ will be a material especially suitable as intercalation electrode in the electrode device according to the invention, the chemical potential of the intercalation electrode being fixed regardless of a change in x due to transport of lithium ions from the ion selective element into the intercalation electrode.

Figure 7:
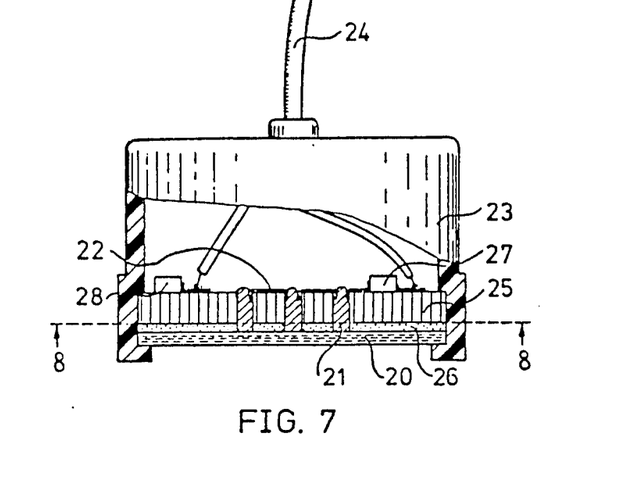
FIG. 7 is a schematic illustration of another embodiment of the measuring electrode device according to the invention.
Figure 8:
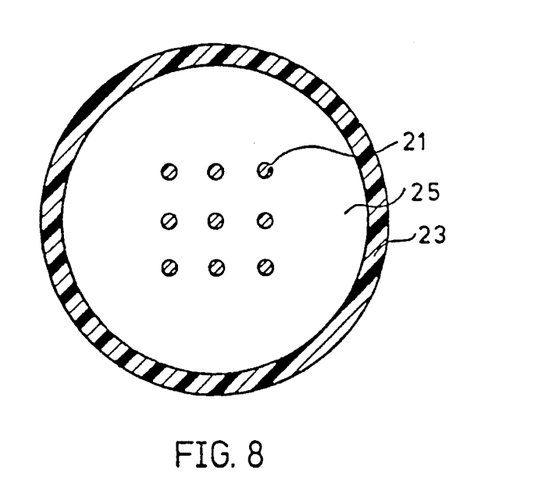
FIG. 8 is a sectional view of the electrode device according to FIG. 7.

The embodiment shown in FIG. 7 is another contemplated construction of the electrode device according to the invention. The construction is compact, rugged and probably suitable for production on a commercial scale.

The embodiment comprises a ceramic substrate 25 having a thermal coefficient of expansion making the substrate compatible with the materials further used in the electrode device. The substrate 25 is provided with a number of through-going passages in which an intercalation compound 21 is provided. An ion selective glass membrane 20 is bonded to a glass layer 26 extending over one side of the substrate and having through-going passages registering with the passages in the substrate 25. The glass layer 26 is made from a relatively low melting glass and the layer is interposed between the membrane 20 and the substrate 25.

Furthermore, the embodiment shown comprises an electrically insulating enclosure 23 to which the substrate 25 and the elements connected therewith are cemented by gluing. The enclosure 23 leaves the main part of the glass membrane 20 exposed to the surroundings To the opposite side of the substrate 25 one or more fields 22 constituting the electrical connection is applied by means of conventional layer technique such as thick or thin film technique, the said field 22 contacting the intercalation compound 21.

Conductor means 24 for connecting the electrode device to a pH-meter or an ion meter is also shown.

Electronic amplifying means 27 and a temperature sensor 28 are also provided in the device according to FIG. 7.

The device according to FIG. 7 may be modified in several ways. E.g. the layer of relatively low melting glass may be omitted, the glass membrane and the substrate then contacting each other directly. Moreover, further suitable electronic components may be integrated in the electrode device.

EXAMPLE 1

Preparation of measuring electrode devices according to the invention

A number of measuring electrode devices according to FIG. 1 were prepared for control of the electrode properties. Electrode devices of similar configuration with the only difference that the tube was a sealed glass tube were prepared, too. Across the seal a platinum wire extended as connected between the spring 5 and the electrode cable 6.

As the intercalation compound $Li_xTiS_2$, $Li_xV_6O_{13}$ and $Li_xV_2O_5$ were tested. As the rod 4 a graphite rod was used in some instances and a steel rod in other instances and as the inert atmosphere argon was used. As the ionic conductive liquid film various combinations of lithium salts in organic solvents were used, e.g. $LiClO_4$ in propylene carbonate.

EXAMPLE 2

Preparation of electrode devices according to the invention

A number of measuring electrode devices of the embodiment according to FIG. 1 were prepared using $Li_2V_6O_{13}$ as the intercalation compound. The electrode devices differed from those of Example 1 therein that the ionic conductive liquid film was replaced by an ionic conductive polymer comprising polyethylene oxide and lithium thiocyanate in the weight ratio 3:1.

This polymer was prepared according to M. B. Armand et al.: Fast Ion Transport in Solids, published by Vashishta, Mundy and Shenoy, Elsevier, 1979, p. 131-136.

100 μl of a 2.6% solution of this polymer in acetonitrile was applied to the inner side of the glass membrane and the solution was evaporated in an argon flow at 50° C.

EXAMPLE 3

Preparing and Testing an Electrode Device according to the Invention

At the end of a glass tube made from lead glass and having an internal diameter of 8 mm a bulb-shaped pH-sensitive membrane having a thickness of 0.2 mm was blown from a pH-sensitive lithium containing silica glass. This glass part corresponds to the glass part of commercially available pH-electrodes manufactured and sold by RADIOMETER A/S, Copenhagen under the trade designation G202C.

Through the open end of the tube 50 mg powdered lithium vanadium bronze of the composition $Li_{0.38}V_2O_5$ was introduced into the tube so as to contact the glass membrane. Subsequently the tube was filled with argon, heated to 600° C. for 1 minute and thereafter slowly cooled to room temperature.

Thereby, the lithium vanadium bronze was sintered to the glass membrane and a two phase system was formed.

A copper conductor was cemented to the lithium vanadium bronze by means of an electrically conductive silver epoxy cement and this conductor was connected to a pH-meter by means of a shielded cable. The electrode device thus prepared corresponds to the device shown in FIG. 2.

The pH electrode device was tested in buffer solutions with varying pH values and the electrical potential was measured at 25° C. by a pH-meter using a standard calomel reference electrode.

The sensitivity was determined to 58.5 mV/pH and in a phosphate puffer of pH 7.00 a potential difference between the electrode device and the reference electrode was determined to 373.3 mV.

An average drift about 0.03 mV/24 hours was found in an experiment wherein measurements were taken in the above-mentioned phosphate buffer over a period of 1 month.

A commercially available glass electrode of the type RADIOMETER G202C having a chloride containing phosphate buffer system as inner liquid and a Ag/AgCl internal reference electrode was tested under the same experimental conditions. An average drift about 0.4 mV/24 hours was found for this device.

It should be understood that the present invention is not limited to the particular construction and arrangement of parts disclosed and illustrated herein, but embraces all modified form thereof that fall within the scope of the following claims.

What is claimed is:

1. An ion selective measuring electrode device comprising an ion selective element having metal ions which during operation of the electrode device are exchanged with other ions of a species to which the ion selective element shows selectivity, the metal ions being of a species different from said other ion species, said ion selective element comprising a glass membrane, an electrical connection, and a solid material for providing electrical contact between the ion selective element and the electrical connection, the solid material comprising a solid crystalline material for incorporating or giving off ions of said metal ion species as an intercalation electrode.

2. The ion selective measuring electrode device according to claim 1, wherein the ion selective element and the solid crystalline material for incorporating or giving off ions of said metal ion species as an intercalation electrode have a common interface which during operation of the electrode device may be crossed by metal ions which the intercalation electrode is capable of incorporating.

3. The ion selective measuring electrode device according to claim 1, wherein the solid material for providing electrical contact between the ion selective element and the electrical connection comprises a two-phase equilibrium mixture, at least one of the phases being said solid crystalline material for incorporating or giving off ions of said metal ion species as an intercalation electrode.

4. The ion selective measuring electrode device according to claim 1, wherein the glass membrane comprises a pH-sensitive glass membrane.

5. The ion selective measuring electrode device according to claim 4, wherein the pH-sensitive glass membrane comprises a pH-sensitive silica glass, said silica glass comprising lithium ions.

6. The ion selective measuring electrode device according to claim 1, wherein the solid crystalline material for incorporating or giving off ions of said metal ion species as an intercalation electrode comprises a bronze of oxide.

7. The ion selective measuring electrode device according to claim 6, wherein the bronze of oxide comprises lithium vanadium bronze.

8. The ion selective measuring electrode device according to claim 7, wherein the lithium vanadium bronze is present as an equilibrium mixture of $\beta$ and $\beta'$ crystals.

9. A method for using a solid material as an intercalation electrode, at least a portion of said solid material comprising a solid crystalline material which incorporates or liberates ions of a metal ion species and is electronically conductive, said method comprising:

incorporating said solid material in an ion selective measuring electrode device, wherein said ion selective measuring electrode device has an ion selective element which contains ions of said metal ion species and shows selectivity towards hydrogen ions or other ion species which differ from said metal ion species, said ion selective element comprising a glass membrane, said ion selective measuring electrode device further comprising an electrical connection, and wherein said solid crystalline material incorporated in said ion selective measuring electrode device acts as a contact material between said ion selective element and said electrical connection so that as the hydrogen ions or other ions are incorporated into said ion selective element, said metal ions are displaced and transferred into said solid crystalline material and electrons necessary for neutralizing the electrical charge in said solid material attributable to the transferred metal ions flow into said solid material from said electrical connection, and when the hydrogen ions or other ion species are liberated from said ion selective element, the metal ions are transferred from said solid crystalline material to said ion selective element and the resulting excess electrons in said crystalline material flow back into said electrical connection.

10. The method according to claim 9, wherein the solid material comprises a two-phase equilibrium mixture, at least one of the phases being said solid crystalline material for incorporating or giving off ions of said metal ion species as an intercalation electrode.

11. The method according to claim 10, wherein the solid crystalline material for incorporating or giving off said ions as an intercalation electrode comprises a bronze of oxide.

12. The method according to claim 9, wherein the solid crystalline material for incorporating or giving off said ions as an intercalation electrode comprises a bronze of oxide.

13. The method according to claim 12, wherein the bronze of oxide comprises a lithium vanadium bronze.

14. The method according to claim 13, wherein the lithium vanadium bronze comprises a two-phase system of $\beta$ and $\beta'$ crystals.

15. The method according to claim 9, wherein the glass membrane comprises a lithium containing silica glass.

16. The method according to claim 15, wherein the glass membrane comprises a pH-sensitive silica glass, said silica glass comprising lithium ions.

17. A method for measuring the hydrogen ion concentration in an electrolyte comprising using a solid material as an intercalation electrode, at least a portion of said solid material comprising a solid crystalline material which incorporates or liberates ions of a metal ion species and is electronically conductive, said solid material incorporated in an ion selective measuring electrode device, wherein said ion selective measuring electrode device has an ion selective element which contains ions of said metal ion species and shows selectivity towards hydrogen ions, said ion selective measuring electrode device further comprising an electrical connection, and wherein said solid crystalline material incorporated in said ion selective measuring electrode device acts as a contact material between said ion selective element and said electrical connection so that as the hydrogen ions are incorporated into said ion selective element, said metal ions are displaced and transferred into said solid crystalline material and electrons necessary for neutralizing the electrical charge in said solid material attributable to the transferred metal ions flow into said solid material from said electrical connection, and when the hydrogen ions are liberated from said ion selective element, the metal ions are transferred from said solid crystalline material to said ion selective element and the resulting excess electrons in said crystalline material flow back into said electrical connection;

and determining the potential difference between said measuring electrode and a reference electrode.

* * * * *